(12) United States Patent
Gullberg et al.

(10) Patent No.: US 8,053,188 B2
(45) Date of Patent: Nov. 8, 2011

(54) NUCLEIC ACID ENRICHMENT

(75) Inventors: Mats Gullberg, Uppsala (SE); Ulf Landegren, Uppsala (SE)

(73) Assignee: Olink AB, Uppsala (SE)

( * ) Notice: Subject to any disclaimer, the term of this patent is extended or adjusted under 35 U.S.C. 154(b) by 711 days.

(21) Appl. No.: 10/495,895

(22) PCT Filed: Nov. 20, 2002

(86) PCT No.: PCT/SE02/02107
§ 371 (c)(1),
(2), (4) Date: Sep. 20, 2004

(87) PCT Pub. No.: WO03/044229
PCT Pub. Date: May 30, 2003

(65) Prior Publication Data
US 2005/0037356 A1 Feb. 17, 2005

(30) Foreign Application Priority Data
Nov. 20, 2001 (GB) .................................. 0127704.5

(51) Int. Cl.
C12Q 1/68 (2006.01)
C07H 21/04 (2006.01)
(52) U.S. Cl. ......................... 435/6.1; 435/6.11; 536/23.1
(58) Field of Classification Search ........................ None
See application file for complete search history.

(56) References Cited

U.S. PATENT DOCUMENTS

| | | | | |
|---|---|---|---|---|
| 5,866,337 | A * | 2/1999 | Schon | 435/6.18 |
| 5,872,105 | A * | 2/1999 | Kool | 514/44 R |
| 6,235,502 | B1 * | 5/2001 | Weissman et al. | 435/91.1 |
| 6,372,424 | B1 * | 4/2002 | Brow et al. | 435/5 |
| 6,558,928 | B1 * | 5/2003 | Landegren | 435/91.1 |
| 6,867,001 | B2 * | 3/2005 | Kondo et al. | 506/17 |
| 2001/0039039 | A1 | 11/2001 | Weissman et al. | |
| 2002/0076704 | A1 * | 6/2002 | Weissman et al. | 435/6 |

FOREIGN PATENT DOCUMENTS

| | | |
|---|---|---|
| WO | 95/22623 A1 | 8/1995 |
| WO | 97/20948 | 6/1997 |
| WO | WO 9949079 | 9/1999 |

OTHER PUBLICATIONS

Lyamichev et al., "Structure-Specific Endonuclease Cleavage of Nucleic Acids by Eubacterial DNA Polymerases," Science, vol. 260, May 7, 1993, pp. 778-783.*
Bonnen et al., "Haplotypes at ATM Identify Coding-Sequence Variation and Indicate a Region of Extensive Linkage Disequilibrium", Am. J. Hum Genet., 67:1437-1451, 2000.
Douglas et al., "Experimentally-derived haplotypes substantially increase the efficiency of linkage disequilibrium studies", Nature Genetics, vol. 28, 361-364, Aug. 2001.
Stephens et al., "Haplotype Variation and Linkage Disequilibrium in 313 Human Genes", Science, vol. 293, 489-493, Jul. 2001.
Drysdale et al., "Complex promoter and coding region β₂-adrenergic receptor haplotypes alter receptor expression and predict in vivo responsiveness", PNAS, vol. 97, No. 19, pp. 10483-10488, Sep. 12, 2000.
Liu et al., "Overlapping PCR for Bidirectional PCR Amplification of Specific Alleles: A Rapid One-Tube Method for Simultaneously Differentiating Homozygotes and Heterozygotes", Genome Research, 7:389-398, Cold Spring Harbor Laboratory Press, 1997.
Ahmadian et al., "Analysis of the p53 Tumor Suppressor Gene by Pyrosequencing", BioTechniques, vol. 28, No. 1, 140-147, 2000.
Kim, et al., "Structural Requirements for FOKI-DNA Interaction and Oligodeoxyribonucleotide-instructed Cleavage," J. Mol. Biol., 258, 638-649, 1996.
Podhajska et al., "Conversion of the FokI endonuclease to a universal restriction enzyme: cleavage of phage M13mp7 DNA at predetermined sites", Gene, 40, 175-182, 1985.
Kool, "Circular Oligonucleotides: New Concepts in Oligonucleotide Design", Annu. Rev. Biophys. Biomol. Struct., 25:1-28; 1996.
Baner et al., "Signal amplification of padlock probes by rolling circle replication", Nucleic Acids Research, vol. 26, No. 22, 5073-5078, 1998.
Lyamichev et al., "Structure-Specific Endonucleolytic Cleavage of Nucleic Acids by Eubacterial DNA Polymerases", Science, vol. 260, 778-783, May 7, 1993.
Landegren et al., "A Ligase-Mediated Gene Detection Technique", Science, vol. 241, 1077-1080, Aug. 26, 1988.
Nilsson et al., "Padlock Probes: Circularizing Oligonucleotides for Localized DNA Detection", Science, vol. 265, 2085-2088, Sep. 30, 1994.
Syvanen et al., "A Primer-Guided Nucleotide Incorporation Assay in the Genotyping of Apolipoprotein E", Genomics 8, 684-692 (1990).
Ronaghi et al., "Real-Time DNA Sequencing Using Detection of Pyrophosphate Release", Analytical Biochemistry, 242, 84-89, Article No. 0432, 1996.
Lyamichev et al., "Polymorphism identification and quantitative detection of genomic DNA by invasive cleavage of oligonucleotide probes", Nature Biotechnology, vol. 17, 292-296, Mar. 1999.
Griffin et al., "Direct genetic analysis of matrix-assisted laser desorption/ionization mass spectrometry", Proc Natl. Acad. Sci. USA, vol. 96, pp. 6301-6306, May 1999.
Heid et al., "Real Time Quantitative PCR", Genome Research, 6, 1054-9803/96, 1996.
Tyagi et al., "Molecular Beacons: Probes that Fluoresce upon Hybridization", Nature Biotechncology, vol. 14, 303-308, Mar. 1996.
Mashal et al., "Detection of mutations by cleavage of DNA heteroduplexes with bacteriophage resolvases," Nature Genetics, 9, 177-183 (1995).
Nishigaki et al, "Type II restriction endonucleases cleave single-stranded DNAs in general," Nucleic Acids Research, 13(16):5747-5760 (1985).
Lyamichev et al, "Structure-specific endonucleolytic cleavage of nucleic acids by eubacterial DNA polymerases," Science, 260:778-783 (1993).
Schena et al, "Quantitative monitoring of gene expression patterns with a complementary DNA microarray," Science, 270:467-470 (1995).
Chee et al, "Accessing genetic information with high-density DNA arrays," Science, 274:610-614 (1996).
Jin et al, "In situ hybridization: methods and applications," Journal of Clinical Laboratory Analysis, 11:2-9 (1997).

* cited by examiner

Primary Examiner — Bradley L Sisson
(74) Attorney, Agent, or Firm — Porter, Wright, Morris & Arthur

(57) ABSTRACT

This invention relates to methods, reagents and kits for enriching nucleic acid sequences. More particularly, the present invention relates to methods, reagents and kits for sample preparation including sample modification, sample enrichment and amplification.

42 Claims, 7 Drawing Sheets

LIGATION TEMPLATE

5' PROTRUDING END

TEMPLATE

GAP OLIGONUCLEOTIDE

FIG. 8A
FIG. 8B
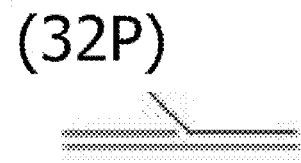
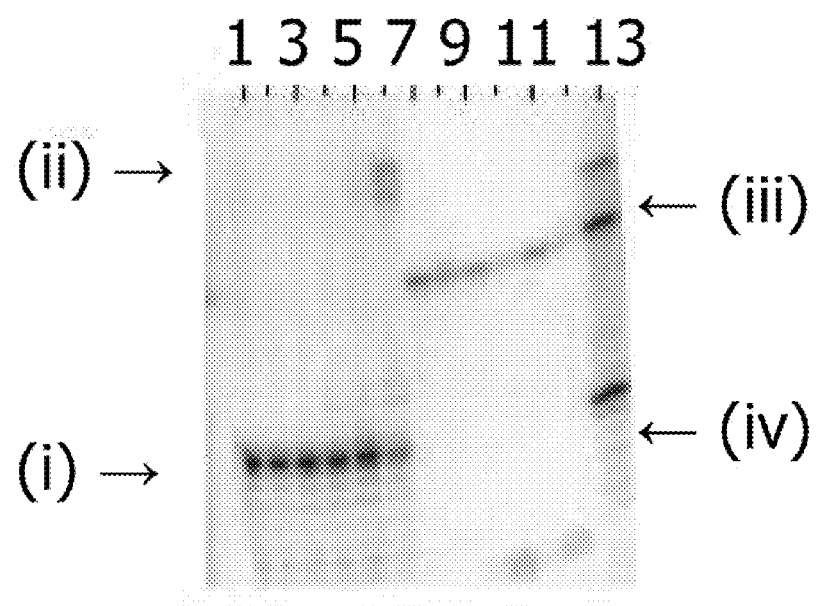
FIG. 8C

NUCLEIC ACID ENRICHMENT

RELATED APPLICATION

The present application is a 371 of PCT/SE02/02107 filed Nov. 20, 2002

FIELD OF THE INVENTION

This invention relates to methods, reagents and kits for enriching nucleic acid sequences. More particularly, the present invention relates to methods, reagents and kits for sample preparation including sample modification, sample enrichment and amplification.

BACKGROUND

Haplotype information can be vital in the analysis of disease by determining whether two or more sequence variants are located on the same nucleic acid fragment. This is of special interest in tumour research and diagnosis where it is important to know if two or more inactivating mutations occur on the same or different chromosomes. Similarly better information about which genotypes are located on the same nucleic acid segment can greatly increase the information derived from genotyping data and in the statistical analysis of genetic linkage or linkage disequilibrium of inherited traits and markers such as single nucleotide polymorphisms, SNPs (e.g. [1-3]).

To date there has been no method developed that satisfactorily solves the problem of how to obtain haplotype information in vitro, that is to determine which gene variants are located, over some distance, on the same nucleic acid molecule.

Current analysis of heritable diseases is hampered by the fact that given the genotypes of the parents, it is still often impossible to confirm if a particular allele is obtained from the mother or from the father. In theory, with the ability to distinguish between haplotypes, more meioses would be informative and thereby facilitate genetic linkage analysis. Another area where haplotyping has proven to be of interest is in the study of genetic effects on a subject's response to different drugs. Recent publications have shown that haplotype information is important to be able to relate genetic factors to a patient's response to various drugs, [4].

Currently, there are only a few methods available for obtaining haplotype information. When lineage data and nucleic acid samples are available linkage analysis is applicable. It is also possible to use statistical methods to calculate possible allele-combinations from allele frequencies to gain information on a haplotype. However, this technique can only be used with a small number of alleles at the same time and on population-size data, and the analysis only provides statistical evidence for the presence of a given haplotype. Haplotype information can also be gained from hemizygous X- and Y-chromosomes, where haplotypes are immediately apparent from the genotype.

The possibility to study cells with only one autosome chromosome is utilised in some in vivo techniques. One approach is the creation of rodent-human hybrid cells, for example using the so called "Conversion technology" [2]. Some of the rodent-human hybrid cells will contain one of the two possible copies from a human chromosome. A second approach is to use hydatidiform moles, i.e. tissues that due to a fertilisation defect only contain genetic material from the sperm (complete hydatidiform mole) thereby containing only one copy of each chromosome.

There are also some in vitro molecular techniques that can be used to determine haplotypes. One technique is the subcloning of all nucleic acid sequences of interest, isolating individual clones and subsequently genotyping them. Allele-specific analysis through Fibre Fluorescent In Situ Hybridisation is another possible approach, however it has not yet been convincingly shown to be useful for SNP based haplotyping. A third approach is double PCR Allele Specific Amplification (double-PASA [5], a double allele-specific Polymerase Chain Reaction (PCR) which gives linkage information of two adjacent polymorphic sites. Pyrosequencing [6] and mass spectrometry may be used to analyse haplotypes over short distances, i.e. <100 nt.

SUMMARY OF THE INVENTION

Methods, reagents and kits to analyse haplotypes, genotypes and enrichment of selected sequences are described herein. These methods and reagents are, in addition to aspects mentioned in the background chapter, also of interest for population genetics, identification of lineage in plant and animal breeding and in analysis of microorganisms.

In one aspect of the invention, a general technique is provided to obtain haplotypes through enrichment for one nucleic acid segment to include a specific variant at a given position. Thereby any variant position in a sample could be used for selection, followed by analysing genetic variants elsewhere in the same nucleic acid fragment.

In another aspect of the invention the same principle can be used for genotyping or to generate probes that reveal the genotype at particular loci.

Accordingly, the present invention provides a method for sample preparation that optionally includes the steps of: (a) cleavage of a nucleic acid so that a fragment containing the sequence to be investigated is created with or without addition of oligonucleotide probes (b) selective modification of one variant of the nucleic acid sequences (c) enrichment of the selected variant, and (d) analysis of the nucleic acid.

The present invention also provides one or several probes for use in the described methods. A first set of probes/probe preferably directs site specific cleavage at predetermined sites of the sample upon hybridisation. Preferably, A second set of probes/probe is used to specifically modify the sample based upon the presence or absence of a given sequence variant. A third set of probes is used for amplification of the sample and a fourth set of probes is used for scoring the genotypes.

The present invention describes several ways to enrich a nucleic acid sequence or sequences from a multitude of sequences on the basis of the sequence or on the basis of a particular sequence variation at a given position.

DETAILED DESCRIPTION OF THE INVENTION

The terms "nucleic acid", "nucleic acid sequence", "nucleic acid fragment", "nucleic acid segment", "nucleic acid probe", "oligonucleotide", "target nucleic acid sequence" or "target sequence" describe interchangeably and without preference, a plurality of nucleotides, covalently linked as such to form linear molecules of DNA or RNA.

The term "variant" describes interchangeably and without preference a nucleic acid encoding a variant, which may for example be selected from the group including any one or more of the following; a single nucleotide sequence variant, deletion sequence variant, insertion sequence variant, sequence length variants, and sequence variation among paralogous or orthologous nucleic acid sequence, or among edited sequences or splice variants Examples of different approaches are as follows.

The first approach, described in part in FIG. 1, is based on cleavage of DNA at any predetermined site through the use of so called nucleic acid adapters, hereafter called adapters, that are targets or part of targets for restriction enzymes preferably type II or type IIs restriction enzymes [7,8]. Adapters and sample are mixed, denatured and subsequently allowed to cool. The adapters hybridise to their complementary regions in the sample nucleic acid. One of the adapters is positioned so that the resulting cleaved sample DNA contains a variant position at the 5' position (A). Added restriction enzymes cleave the sample and, through addition of a ligation template that anneals to both the 5' and 3' end of the cleaved sample DNA, circular molecules are obtained by ligation of the ends that are brought next to each other (B). This circularisation is driven by the higher relative concentration of two ends belonging to the same molecule compared to those of two different copies of the same or similar molecules. If the added template is complementary to the sample DNA-ends, juxtaposing these, then ligation of the two ends can occur. If a mismatch between the sample DNA and the ligation template exists at the variant position used for selection, or if there are no free ends at the site intended for ligation, then ligation will not occur. Circularised molecules can then be enriched for through the use of exonucleases that degrade uncircularised DNA, and/or amplification of the circularised DNA, for example with rolling circle amplification (RCA) can be performed ([9,10]).

Alternatively, the adapter could be positioned upstream of the variant position used for selection. Optionally this adapter could be completely omitted. After cleavage, as described earlier, one or a plurality of oligonucleotides is added, (template), which hybridises to both the 3' end and to an upstream sequence around the variant position, as shown in FIG. 2A. This provides a specificity step. The structure is then cleaved by chemical, enzyme or other means to generate a structure, as shown in FIG. 2B. Where an enzyme is used, any enzyme capable of cleaving such a structure may be used [11]. The enzyme is preferably selected from, FEN nuclease, Mja nuclease, native or recombinant polymerase from *Thermus aquatiqus, Thermus thermophilus,* or *Thermus flavus,* or any enzyme selected according to the teachings of Lyamichev et al [11] or U.S. Pat. No. 5,846,717, which are incorporated herein by reference. The variant position used for selection can either be removed by cleavage, or the cleavage can be performed so that the variant position is the 5'-most nucleotide of the sequence. Hence the major selective step is in the subsequent ligation reaction. The use of nucleic acid ligation for allele distinction is well described in the literature, for example [12,13]. To ensure that the cleaved substrate is eligible for ligation the 3' sample nucleotide must be complementary to the added template. This can be achieved directly from cleavage of the sample, in which case it is possible to ligate the DNA directly.

Another approach, which confers increased specificity, is to construct the added template so that it contains one extra nucleotide, giving a gap between the hybridised 3' and 5' sequences, similar to that observed for the SNP. By adding only the complementary nucleotide to the cleavage reaction a substrate for cleavage will only be generated from nucleic acid sequences that contain the complementary nucleic acid sequence.

Yet another approach is to construct the added template so that there will be a gap. This gap may be filled in by the addition of a complementary oligonucleotide, as shown in FIG. 2C. Optionally, this gap filling oligonucleotide can be labelled with an affinity tag, for example a specific sequence or specific molecule for subsequent affinity purification. The gap filling oligonucleotide can also be of a specific sequence to be used for circular DNA amplification as described in co-pending application PCT/SE02/01378.

Cleavage of the sample DNA can also be achieved with restriction enzymes through the addition of oligonucleotides that hybridise to the selected sequence. The 5' cleavage site may or may not be influenced by the variable sequence. Circularisation and selection is then conducted via any of the above-mentioned approaches.

Instead of circularising the DNA, the nucleic acid fragment ends can be protected via addition of protecting adapters to one or both ends based on selective addition at a variant position at at least one of the ends, as shown in FIG. 3. Generation of the 3' or 5' sample ends could be achieved either through cleavage at the variable position or upstream at a generic site, as previously described. In the latter case cleavage will be performed via structure-specific cleavage as previously described. This protected linear substrate can now be enriched for, through degradation of unprotected sample using exonucleases. Selective amplification of the protected allele can be performed based on the presence of the added sequence/sequences.

It is not necessary to generate restriction sites in the sample or to denature double stranded DNA. Any number of restriction enzymes having recognition sequences located on either side but not within the sequence of interest, can be used.

Double stranded DNA can be digested at a multitude of sites with one or several different restriction enzymes. Digestion at one or several of the sites may or may not be affected by a sequence variant. If one specific sequence variant affects digestion by a restriction enzyme at a given site, only one of the alleles will become circularised upon ligation with a ligation template in the form a ligation casette. A ligation cassette consists of a pair of prehybridized complementary oligonucleotides with single stranded sequences protruding at one or both ends to form a correct ligation site for the chosen sequences to be ligated. Only the circularised allele becomes a template for circular amplification by e.g. rolling circle amplification. If the sample is kept double stranded throughout the process the RCA amplified allele will be the only single stranded DNA in the sample. This single stranded DNA can then be genotpyed by a single strand specific genotyping method such as, including by way of example only, padlock probes, oligonucleotide ligation assay or invader assay. The principle of specifically generate only a subset of a sample single stranded can be utilized with any method capable of performing such an action and is not to be limited to the one mentioned. Subsequent analysis with single strand specific methods reveals the genotype of only the selected, and thus single stranded sequence.

In one version an exonuclease is added to make one or both ends of a restriction enzyme digested double stranded sample partially single stranded before circularization. A chosen specific sequence is circularized, templated by an added oligonucleotide or pairs of oligonucleotides either directly or via a structure-specific enzyme cut, as described above, followed by specific ligation. The strands are then gap-filled, followed by DNA ligation. Only the correct allele can be made into a complete circle possible to amplify with RCA.

A further variant to generate single stranded DNA from a restriction enzyme digested of a double stranded sample is to specifically degrade only one of the strands with exonucleases. This can be achieved, by way of example only, through making a proper choice of restriction enzymes that will produce a sticky end that is not a substrate for the chosen exonuclease or exonucleases; or via DNA ligation adding a protecting sequence to one or both of the ends; or via DNA ligation add a chemically modified and protected sequence to one or both of the ends. The single stranded DNA can then be circularized, either directly via specific ligation or via a structure-specific enzyme cut followed by specific ligation as previously described.

It is also possible to circularise double stranded DNA with or without the addition of a ligation cassette, as described earlier, to make one of the strands so it can prime an RCA with the intact circularised strand as template. After a predefined time the polymerase is inactivated and an oligonucleotide complementary to a specific part of the amplification product is added so that it creates a restriction enzyme site in one of the alleles. After restriction enzyme digestion the digested allele is recircularised, according to the description in co-pending application PCT/SE02/01378, making it resistant to exonuclease degradation. After exonuclease treatment, serving to degrade all linear nucleic acids and thereby avoiding branched amplification of the non-circularized allele, a second generation RCA is conducted, primed with a second oligonucleotide, effectively amplifying only the circularised allele.

The enriched sample can be subjected to genotyping through any method and compared to results from genotyping of the total sample. Examples of methods which may be used are oligonucleotide ligation assays [12], padlock probes [13], primer extension assays [14], pyrosequencing [15], invader technology [16], mass-spectroscopy [17] or homogenous PCR methods e.g. Taqman [18] or molecular beacons [19]. However, other methods may be employed with equal utility. By using the enriched sample instead of a whole sample as the test sample it is also feasible to use any suitable method-, to find new/unknown mutations or polymorphisms. Thereby all possible mutations in the enriched segment may be detected, also unknown ones, for example by Sanger sequencing or by hybridising the enriched sample to an array in order to resequence the sample and in this respect also find new or unknown mutations. The methods could be, but are not limited to the use of, mismatch recognising enzymes for example T4 endo VII [20], DHPLC resequencing, Sanger or array, or pyrosequencing [15]. However, other methods may be employed with equal utility. The resulting genotypes will reveal the specific haplotype of the sample.

Accordingly, the present invention provides one or several sets of probes. A first set of probes/probe direct site specific cleavage at predetermined sites of the sample upon hybridisation. A second set of probes/probe is used to specifically modify the sample based upon a sequence variant. A third set of probes is used for amplification of the sample and a fourth set of probes is used for scoring the genotypes.

Instead of investigating the genotypes all along the selected nucleic acid one can use the same principle for genotyping the variant position used for selection. Upon cleavage of sample DNA an oligonucleotide can be added that anneals to the 3' end of a generated fragment and to a stretch upstream, around the variant position to be scored, so that a probe with a hybridising region at its 5' end is formed, (as shown in FIG. 4A), or a probe with a non-hybridising region at its 5' end is formed, (as shown in FIG. 4B). If necessary this structure can then be cleaved as previously described. The use of ligase will complete the nucleic acid circle. The circle can then be enriched for, using exonuclease treatment and nucleic acid amplification, preferably rolling circle amplification. Preferentially the oligonucleotide added contains a sequence between the 3' and the 5' hybridising end that consist of a selected sequence used for later hybridisation that can be rendered double stranded through the addition of a second oligonucleotide, shown in FIG. 4A as object 1. The added oligonucleotide could contain a recognition sequence for a type IIs restriction enzyme and preferably a sequence as dissimilar as possible compared to other oligonucleotides used for other loci, as described in co-pending application PCT/SE02/01378, the contents of which are incorporated herein by reference. Detection of the circularised nucleic acid or amplification products templated by the circularised nucleic acid is used to score the genotype of the selected position.

Due to the intramolecular nature of the ligation reaction it is feasible to perform many reactions at the same time (from one to several tens of thousands). At any practical concentration the fragments will circularise intramolecularly in preference to intermolecular reactions.

Accordingly, the present invention further provides one or a set of probes. A first set of probes/probe directs site-specific cleavage at predetermined sites of the sample upon hybridisation. A second set of probes/probe is used to specifically modify the sample based upon a sequence variant. A third set of probes is used for amplification of the enriched sample.

The variant position could be, but is not limited to a sequence variant polymorphism which may be selected from the group including any one or more; deletion variant, insertion variant, sequence length variant, single nucleotide polymorphism, substitution variant, paralogous or orthologous nucleic acid sequences, edited sequences or splice variants.

The present invention is also to be used as a mean to isolate and enrich for a specific sequence or sequences among a multitude of sequences, with the intention of further manipulation of the enriched sequence/sequences. The methods could be any, sole or a combination of but not limited to, amplification, quantification, sequencing, variant scoring, using the enriched sequence/sequences as probes or to compare different enriched samples on the basis of for example amount of sample.

Accordingly, the present invention further provides one or a set of probes. A first set of probes/probe directs site specific cleavage at predetermined sites of the sample upon hybridisation. A second set of probes/probe is used to specifically modify the sample based upon a nucleotide sequence. A third set of probes is used for amplification of the enriched sample.

In all of the above-mentioned methods where DNA samples are mentioned they could be exchanged with RNA or cDNA samples.

An added oligonucleotide probe can also be treated by the same principles and to be used for subsequent genotyping, as shown in FIG. 5, if the added oligonucleotide anneals forming a non-hybridising region at the 5' end. Cleavage of this structure will generate a molecule that can be circularised with a ligase. Ligation will depend on whether the 5' nucleotide is matched or not with the sample. This circularised probe can then be detected either directly or via the presence of amplification products (based on the presence of the circle or amplification products of the circle). The presence of such a product describes the nature of the variant position. The added oligonucleotide could preferentially contain a molecule or sequence in the 5' part that is used as an affinity tag for removal of unmodified circles before amplification of the circularised probes.

Accordingly, the present invention provides one or a set of probes. A first set of probes to be specifically modified based on the nature of a nucleotide in the target nucleic acid. A second set of probes could be used for purification of the sample. A third set of probes is used for amplification of the modified probes.

Embodiments of the invention will now be described in greater detail, by way of example only not in any way to limit the invention, with reference to the accompanying drawings, of which;

Figure 9:
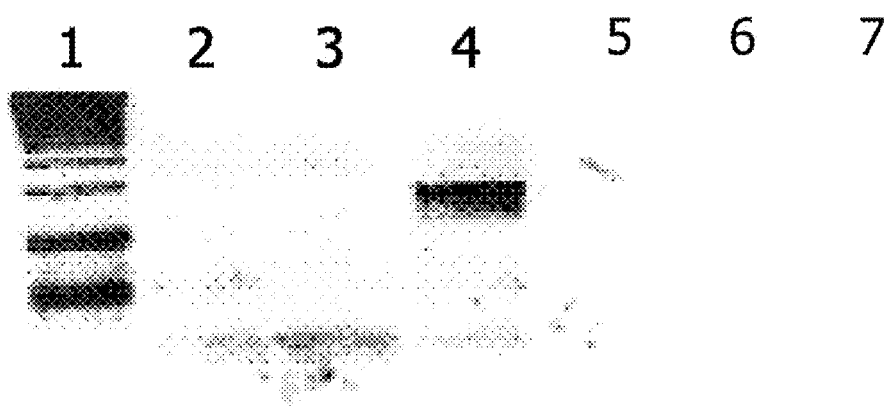

FIG. 8 is showing an image of a poly acrylamide gel of radioactive labelled nucleic acids showing cleavage and ligation of structure specific cleaved nucleic acids with native DNA Taq polymerase and Tth ligase; and FIG. 9 is showing a photo of an ethidium bromide stained gel of amplification products obtained from an experiment with cleaved BAC DNA that had been circularised via cleavage by a structure specific enzyme and the two ends joined by a ligase.

EXAMPLES

Example 1

Circularisation of DNA after cleavage with restriction enzymes followed by enrichment through exonuclease treatment and rolling circle amplification. (See FIG. 4)

A BAC clone (RP11-381L18, BacPac resources, Children's hospital, Oakland) with a genomic fragment containing the gene ATP7B was used. DNA was isolated by the rapid alkaline lysis miniprep method and the DNA concentration was determined measuring UV $A_{260}$.

HpaII 5 U (New England Biolabs) was used to cleave a double stranded (ds) template in buffer (10 mM Tris-HCl pH 7.5, 10 mM $MgCl_2$, 1 mM DTT) for 2 hours at 37° C. before heat-inactivation of the enzyme. Two pmol of the ds template was cleaved with HpaII. After the cleavage, the reaction was diluted to different concentrations ($10^4$-$10^8$ molecules/µl).

The template was ligated into a circle using 0.5 units of T4 DNA ligase, 1×T4 DNA ligase bf (66 mM Tris-HCl pH 7.6, 6.6 mM $MgCl_2$, 10 mM DTT, 66 µM ATP) and 10 nM ligation template, 5'Biotin-tt ttt ttt ttt ttt gtc tgg aaa gca aac cgg tgc cca ccc atg a 3' SEQ ID NO1, in each reaction. After denaturation and subsequent addition of ligase to half of the reactions (see below), the samples were incubated at 37° C. for 30 min and then the ligase was heat-inactivated at 65° C. for 20 minutes After ligation, the samples were treated with exonucleases. Exonuclease V (5 units) was used for 30 min 37° C. before heat-inactivation. The result was detected by performing a PCR with the following primers, 5 acg ccc acg gct gtc at 3' SEQ ID NO2 and 5' tgg acg tct gga aag caa a 3' SEQ ID NO3, (1 µM) located on both sides of the ligation junction. In 50 mM Tris HCl pH 8.3, 50 mM KCl, 200 µM dNTP, 0.125 u Taq GOLD polymerase (Perkin Elmer), 0.08×SYBR Green (Molecular Probes) as reporter molecule, and 1×ROX (Molecular Probes) as standard, temperature cycles as follows 95° C. 10 min activation of Taq polymerase followed by 40 cycles of 95° C. 20 sec, 52° C. 1 min, 72° C. 20 sec. The experiments yield a cycle threshold value, Ct which is inversely proportional to the amount of starting material in the sample.

After the PCR amplification the reactions products were electrophoresed in a 3% agarose gel to ensure that a product of the correct length had been produced.

Figure 1A:
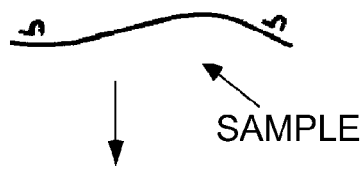
FIG. 1 is a schematic representation of cleavage and circularisation of sample nucleic acid through the use of adapters.
Figure 1B:
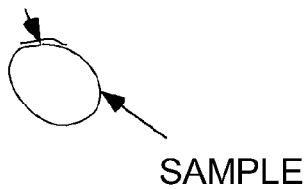
Figure 2A:
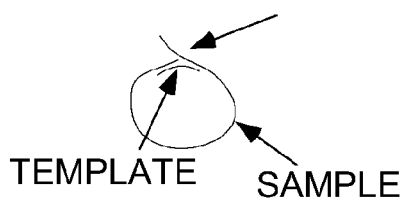
FIG. 2 is a schematic representation of structure specific cleavage for circularisation of sample nucleic acids.
Figure 2B:
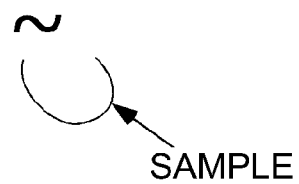
Figure 2C:
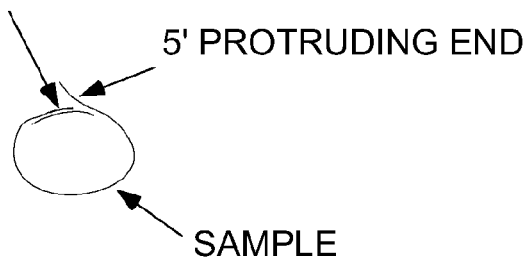
Figure 3:
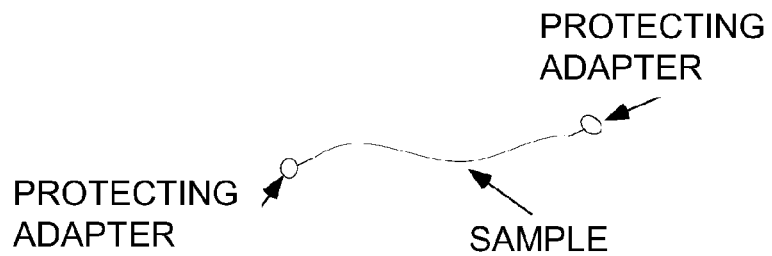
FIG. 3 is a schematic representation of addition of protecting ends to a linear nucleic acid sample.
Figure 4A:
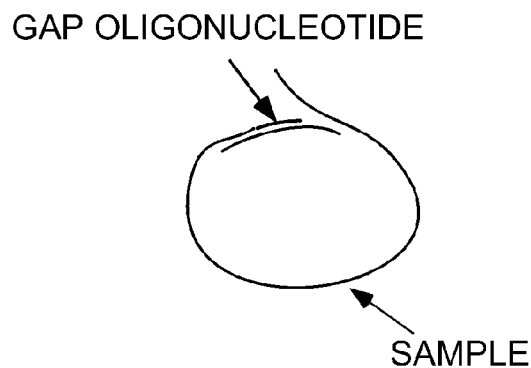
FIG. 4 is a schematic representation of the use of gap-oligonucleotides for circularisation of sample nucleic acids.
Figure 4B:
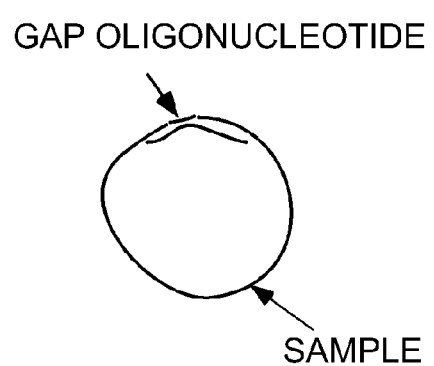
Figure 5:
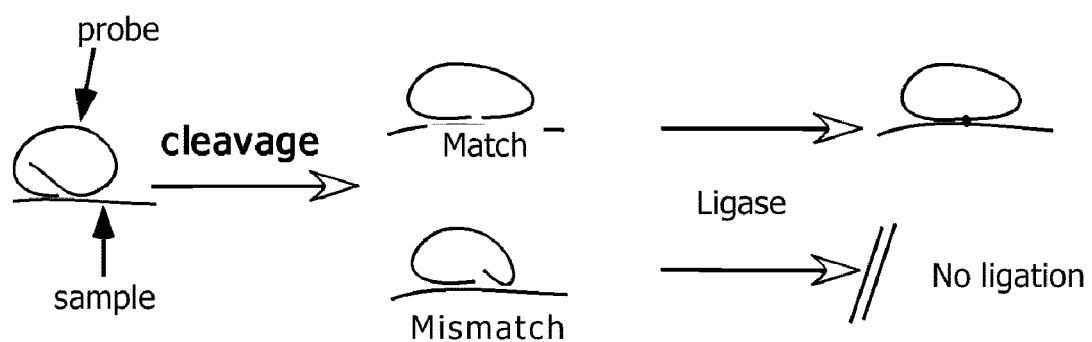
FIG. 5 is a schematic representation of scoring SNPs through circularisation of nucleic acid probes.

The results are shown in FIG. 4, where A) Graph showing the fluorescence readings from a real-time PCR experiment read in an ABI 7700. The figures to the left corresponds to the numberings in B. Reactions were as follows; #2, 3—No template control, #4 sample+ligase, #5 Sample−ligase, #6 sample+ligase+RCA, #7 Sample−ligase+RCA B) A 3% agarose gel of the PCR reactions shown in A. Lane 1 in B is loaded with a 100 bp-ladder (lowest band around 50 bp). Lane 2-7 corresponds to the same reactions. The arrow denotes the size for a correct length product.

Example 2

Enrichment of circular DNA over non-circular DNA through the use of different exonucleases.

BAC DNA as described in example 1 were cleaved and ligated as described in EXAMPLE 1. Half of the sample was ligated with T4 DNA ligase and half of the sample was not. The two reactions were further divided into five different reactions of each (+/−ligase) treated as follows.

1. 5 u ExoV and 1 mM ATP,
2. 5 u ExoI, 50 u ExoIII and 25 u T7gene6
3. 5 u ExoI 50 u ExoIII and 2.45 u Lambda exo
4. 50 u ExoIII, 0.5 u ExoVII and 2.45 u Lambda Exo
5. 5 u ExoI, 0.5 u ExoVII in 1×Tris buffer All reactions were incubated at 37° C. for 30 minutes before heat inactivation of the nucleases at 80° C. for 20 minutes. The results were determined as described in example 1. After the PCR amplification, the reaction products were electrophoresed in a 3% agarose gel, and the nucleic acid visualised to ensure that a product of the correct length had been produced (not shown). The results are shown in table 1.

TABLE 1

Shows the result from an exonuclease treatment of cleave DNA that had been or had not been circularised with ligase.

| Exo treatment: | +ligase: Ct value | −ligase: Ct value |
|---|---|---|
| ExoV(5 U) + ATP(1 mM) | 24.49 | 35.82 |
| ExoI (5 U) + ExoIII (50 U) + T7Gen6 (25 U) | 21.33 | 33.52 |
| ExoI (5 U) + ExoIII (50 U) + λExo (2.45 U) | 21.52 | 35.07 |
| ExoIII (50 U) + ExoVII (0.5 U) + λExo (2.45 U) | 22.85 | 35.70 |
| ExoI (5 U) + ExoVII (0.5 U) + 1× Tris bf | 28.05 | 34.70 |

Example 3

Figure 7A:
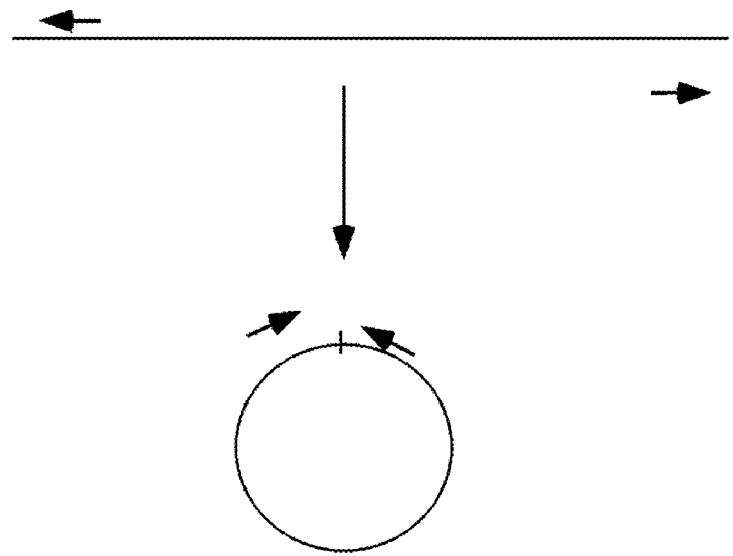
FIG. 7 is a schematic representation (A) of the experimental set-up for detection of circularisation of nucleic acids via inverse PCR and (B) a photo of an agarose gel showing the result of such an experiment where BAC DNA cut with FokI adapters, circularised with ligase, circular molecules enriched for via exonucleases and finally used for template in an inverse PCR reaction.
Figure 7B:
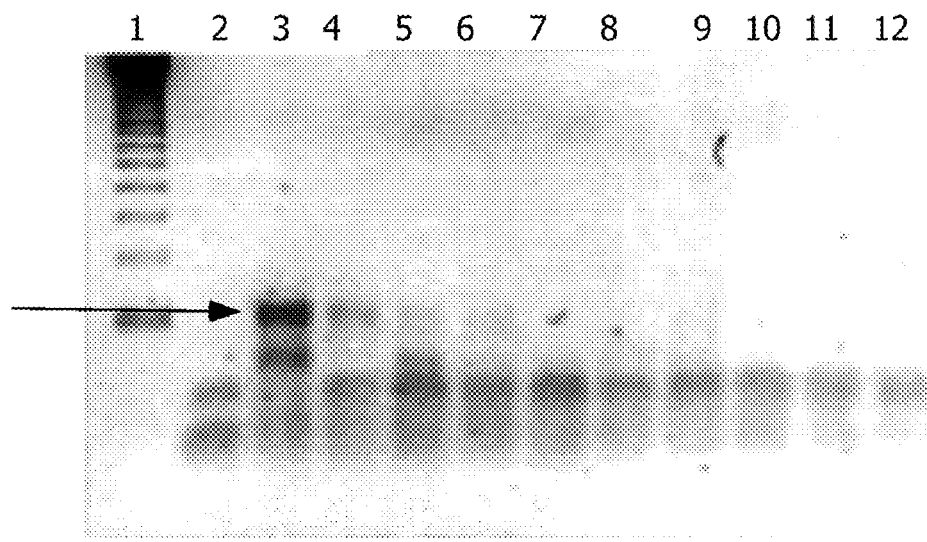

Circularisation of DNA after denaturation of dsDNA, hybridisation of FokI adapters, cleavage of the DNA at pre-determined sites, specific circularisation of the cleaved fragment based on an SNP at the 5'prime end and enrichment of the circularised DNA. (See FIG. 7)

BAC DNA was purified as described in example 1.

BAC DNA was diluted in a series and denatured by heat. After denaturation the samples were directly put on ice.

Different amounts ($10^1$-$10^{10}$ molecules) of BAC DNA were cleaved with 2 units FokI and 2 fmol FokI adapters (FokI adapter 5'UTR 5' cgc atc cca cgt ggg atg cga aag caa aca ggg gt 3' SEQ ID NO4, FokI adapter C2930T C-allele 5' gcc atc cgt gca cgg atg gct gca cag cac cgt gat 3' SEQ ID NO5, FokI adapter C2930T T-allele 5' gcc atc cgt gca cgg atg gct gca cag cac cat gat 3' SEQ ID NO6) in 10 mM Tris-HCl pH 7.5, 10 mM MgCl$_2$, 1 mM DTT, 50 mM NaCl, 1×BSA1 for 2 hours 37° C. before heat-inactivation of the enzyme.

The ends of the generated fragment nucleic acid were ligated into a circle using 8 fmol of the correct/incorrect ligation template (20+20 WDgDNA 5'UTR-Ex13 C-allele, 5' ctc ggc tct aaa gca aac agg tga tgg acg tct gga aag ctt t 3' SEQ ID NO7, 20+20 WDgDNA 5'UTR-Ex13 T-allele 5' ctc ggc tct aaa gca aac aga tga tgg acg tct gga aag ctt t 3' SEQ ID NO8). One unit T4 DNA ligase and 1×T4 DNA ligase buffer was used, and the reactions were incubated for approximately 30 minutes at 37° C. before heat-inactivation of the DNA ligase. The circles were exonuclease treated with 5 units ExoV and 1 mM ATP and the samples were incubated in 37° C. for 30 min before heat-inactivation at 80° C. for 20 minutes.

PCR amplification was performed with primers (Frw WDgDNA 5'UTR-Ex13 5' cag agg tga tca tcc ggt ttg 3' SEQ ID NO9, Rew WDgDNA 5'UTR-Ex13 5' gga gag gag gcg cag agt gt 3' SEQ ID NO10), 0.5 µM of each, located on both sides of the ligation junction. With a total volume of 50 µl, 200 µM dNTP, 1 unit Taq GOLD polymerase, 1×PCR buffer (10 mM Tris-HCl pH 8.3, 50 mM KCl, 1.5 mM MgCl$_2$, 0.001% (w/v) gelatine). 40 amplification cycles were run after activation of the polymerase: 95° C. 15 sec, 58° C. 1 min and 72° C. 20 sec. The amplified nucleic acids were detected by electrophoresis in a 3% agarose gel and visualisation by staining with ethidium bromide.

Figure 6A:
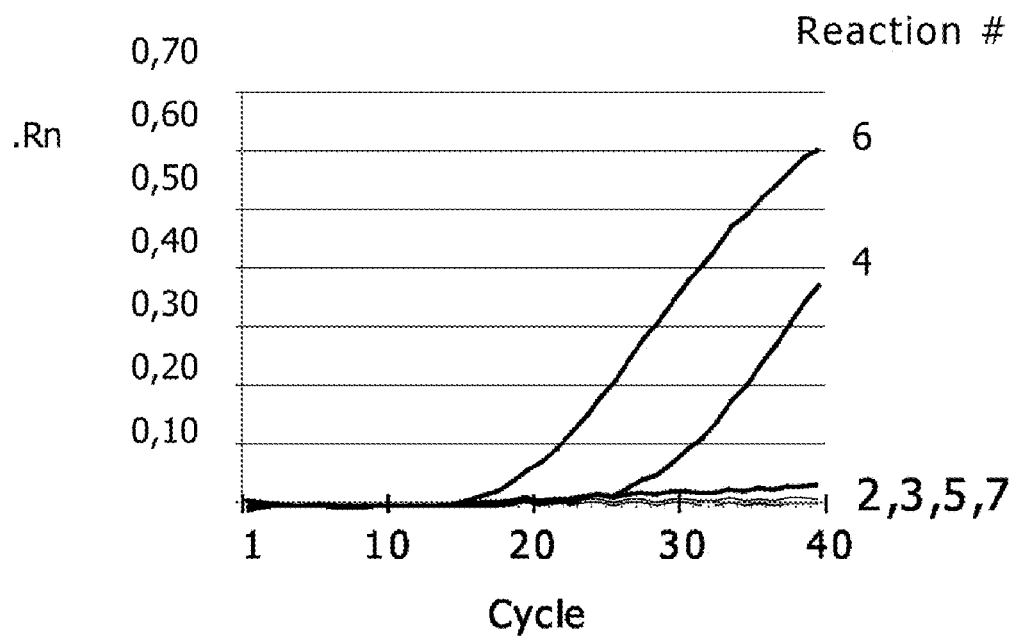
FIG. 6 shows (A) the result from a real-time PCR experiment and (B) the gel of the same amplification reactions from an experiment of cleaving, ligating and rolling circle amplification of BAC DNA.
Figure 6B:
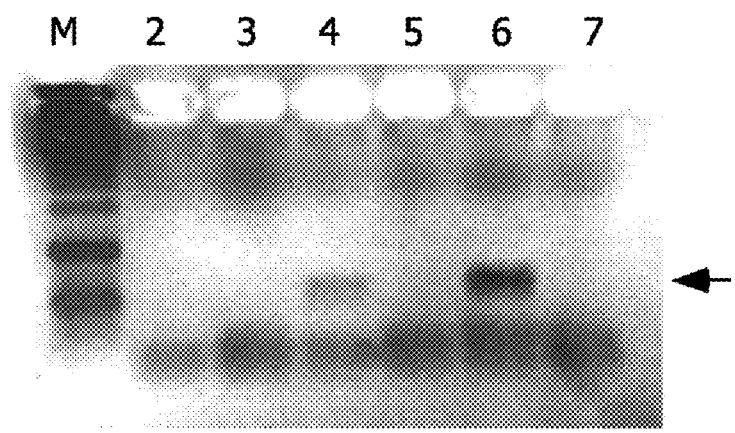

The results are shown in FIG. 6B. The following samples were loaded into the different lanes; 1—Marker, 2 No template control, 3-8 samples from a 10-fold dilution series ($10^{10}$-$10^{1}$) of BAC DNA with correct ligation template and ligase, 9 sample with correct ligation template but minus ligase, 10-12 samples from a 10-fold dilution series (10e10 to 10e9) with a ligation template corresponding to the wrong allele, T instead of C). The arrow denotes the size of a correct length product.

Example 4

Selective ligation of oligonucleotides cleaved with a structure specific enzyme. (See FIG. 8)

The reactions were performed in 1×Tth buffer (1 mM NAD, 10 mM DTT and 0.1% Triton X-100). 20 µl reactions containing 0.5 pmol of the upstream, downstream and target oligonucleotides respectively (primer22+1 5' gta ttt gct ggg cac tca ctg ca 3' SEQ ID NO11, ArmC 5' tcc aga cgt cca tca cgg tgc tgt gca ttg cct g 3' SEQ ID NO12 or ArmT 5' tcc aga cgt cca tca tgg tgc tgt gca ttg cct g 3' SEQ ID NO13, Template2930 5'cag gca atg cac agc acc gtg cag tga gtg ccc agc aaa tac3' SEQ ID NO14), 1 unit of Tth ligase and native Taq polymerase. The reactions were prepared on ice and initiated by transfer to a Thermal Cycle where the following program was run: 95° C. 20 sec, 72° C. 30 min for 2 cycles. The upstream or downstream oligonucleotide was radio labelled and the samples were analysed on a 10% denaturing polyacrylamide gel. Ten pmol target DNA was end-labelled with 1.65 pmol γ-$^{32}$P dATP (NEN). 4.9 U T4 PNK enzyme and 1×T4 PNK buffer (0.05 M Tris-HCl pH 7.6, 10 mM MgCl$_2$, 10 mM 2-mercaptoethanol) was added to each labelling reaction and the tubes were incubated for 45 min in 37° C. EDTA (1 mM) was added and the samples were boiled for 5 min in a water bath. The unincorporated nucleotides were removed from the labelling reaction with a MicroSpin™ G-50 column (Amersham Pharmacia Biotech).

The experiments with the radio labelled oligonucleotides were detected on a 10% polyacrylamide gel containing 7 M UREA. The gel was run with 0.5×Tris Borat EDTA buffer at 30 W for approximately 30 min and was dried in a gel dryer for 2 hours 80° C. The dried gel was exposed to a phosphorimager screen overnight.

The results are shown in FIG. 8. Oligonucleotides yielding structure A was used in experiments 1-6 and oligonucleotides yielding structure B was used in experiments 7-12. (i) denotes the size of un-reacted oligonucleotide in experiments 1-6, (ii) the size for ligated product in reactions 1-6, (iii) uncleaved oligonucleotide used in reactions 7-12 and (iv) cleaved oligonucleotide in reactions 7-12. 32P denotes a radioactive label on respective oligonucleotide.

Lanes 1-6 shows the results from experiments with oligonucleotide 1 labelled with $^{32}$P. Lane 1, T-allel (wrong)—Taq polymerase, lane 2 C-allel (correct)—Taq polymerase, lane 3 T-allele—Tth ligase, lane 4 C-allel—Tth ligase, lane 5 T-allel, lane 6 C-allele.

Lanes 7-12 show the results from experiments with oligonucleotide 2 radio labelled with P$^{32}$ Lanes 7, 9, 11 is with the T-allele (incorrect) and lane 8, 10, 12 is with the C-allele (correct). Lanes 7-8 minus Taq polymerase, lanes 9-10 minus Tth ligase.

Lane 13 shows size markers.

Example 5

Circularisation of BAC DNA after cleavage with restriction enzymes, intramolecular hybridisation and cleavage with a structure specific enzyme followed by ligation, as shown in FIG. 9.

BAC DNA was purified as described in example 1.

Denatured, ss BAC DNA (1×$10^{10}$ molecules) was cleaved with 10 units DraIII in buffer (10 mM NaCl, 5 mM Tris-HCl, 1 mM MgCl$_2$, 0.1 mM DTT pH 7.9) was used. DraIII was allowed to cleave the DNA for 1 hour 37° C. before heat-inactivation.

This experiment was also done with genomic DNA. $10^{10}$ molecules were cleaved by 1 pmol of each adapter (cleave DraIII up2930 5' act gga cac aac gtg acg aac ttg ggt 3' SEQ ID NO15 and cleave DraII down2930 5' cag ggc tca cac gca gtg agt gcc c 3' SEQ ID NO16) designed to hybridise to sequences in exon 13. The subsequent concerted structure-specific cleavage and ligation reaction contained the same reagents as above and 2 pmol of ligation any of two different templates (20+20 DraIII-C 5' taa acg acc cgt gag tga cgc aca ggt cac ggg ggg ac 3' SEQ ID NO17 or 20+20 DraIII-G 5' taa acg acc cgt gag tga cgg aca ggt cac ggg ggg ac 3' SEQ ID NO18). The samples were divided into two parts and on one half was subjected to a RCA. A real-time PCR was performed on the samples with primers located on both sides of the ligation junction. In a total volume of 50 µl the following reagents were included: 2.5 µl sample, 1×PCR bf, 100 µM dNTP, 1 unit Taq GOLD polymerase, 0.5 µM of each primer, 1×ROX and 0.08×SYBR. After activating the polymerase 95° C. for 10 min, 40 cycles of the following program was run in a Thermal Cycler: 95° C. 20 sec, 58° C. 1 min and 72° C. 30 sec.

DraIII and specific adapters designed to hybridise to sequences in exon 13 of ATP7B cleaved BAC DNA at predetermined sites. The target DNA was denatured to become single-stranded and the adapters were designed to create recognition and cleavage sites for DraIII. DraIII cleavage created a substrate that was used in the structure-specific cleavage, which generated the 5' located SNP.

The results are shown in FIG. 8. Shown is the samples run on a 3% agarose gel. Lane 1 is a size marker, lane 2 and 3 PCR no template controls, lane 4 sample, lane 5 without Taq polymerase, lane 6 without Tth ligase and lane 7 without BAC DNA.

REFERENCES

1. Bonnen P E, Story M D, Ashorn C L, Buchholz T A, Weil M M, Nelson D L: Haplotypes at ATM identify coding-sequence variation and indicate a region of extensive linkage disequilibrium. *Am J Hum Genet* 2000, 67:1437-1451.
2. Douglas J A, Boehnke M, Gillanders E, Trent J M, Gruber S B: Experimentally-derived haplotypes substantially increase the efficiency of linkage disequilibrium studies. *Net Genet* 2001, 28:361-364.
3. Stephens J C, Schneider J A, Tanguay D A, Choi J, Acharya T, Stanley S E, Jiang R, Messer C J, Chew A, Han J H, et al.: Haplotype variation and linkage disequilibrium in 313 human genes. *Science* 2001, 293:489-493.
4. Drysdale C M, McGraw D W, Stack C B, Stephens J C, Judson R S, Nandabalan K, Arnold K, Ruano G, Liggett S B: Complex promoter and coding region beta 2-adrenergic receptor haplotypes alter receptor expression and predict in vivo responsiveness. *Proc Natl Acad Sci USA* 2000, 97: 10483-10488.
5. Liu Q, Thorland E C, Heit J A, Sommer S S: Overlapping PCR for bidirectional PCR amplification of specific alleles: a rapid one-tube method for simultaneously differentiating homozygotes and heterozygotes. *Genome Res* 1997, 7:389-398.
6. Ahmadian A, Lundeberg J, Nyren P, Uhlen M, Ronaghi M: Analysis of the p53 tumor suppressor gene by pyrosequencing. *Biotechniques* 2000, 28: 140-144, 146-147.
7. Kim S C, Skowron P M, Szybalski W: Structural requirements for FokI-DNA interaction and oligodeoxyribonucleotide-instructed cleavage. *J Mol Biol* 1996, 258:638-649.
8. Podhajska A J, Szybalski W: Conversion of the FokI endonuclease to a universal restriction enzyme: cleavage of phage M13 mp7 DNA at predetermined sites. *Gene* 1985, 40:175-182.
9. Kool E T: Circular oligonucleotides: new concepts in oligonucleotide design. *Annu Rev Biophys Biomol Struct* 1996, 25:1-28.
10. Baner J, Nilsson M, Mendel-Hartvig M, Landegren U: Signal amplification of padlock probes by rolling circle replication. *Nucleic Acids Res* 1998, 26:5073-5078.
11. Lyamichev V, Brow M A, Dahlberg J E: Structure-specific endonucleolytic cleavage of nucleic acids by eubacterial DNA polymerases. *Science* 1993, 260:778-783.
12. Landegren U, Kaiser R, Sanders J, Hood L: A ligase-mediated gene detection technique. *Science* 1988, 241.
13. Nilsson M, Malmgren H, Samiotaki M, Kwiatkowski M, Chowdhary B P, Landegren U: Padlock probes: circularizing oligonucleotides for localized DNA detection. *Science* 1994, 265:2085-2088.
14. Syvanen A C, Aalto-Setala K, Harju L, Kontula K, Soderlund H: A primer-guided nucleotide incorporation assay in the genotyping of apolipoprotein E. *Genomics* 1990, 8:684-692.
15. Ronaghi M, Karamohamed S, Pettersson B. Uhlen M, Nyren P: Real-time DNA sequencing using detection of pyrophosphate release. *Anal Biochem* 1996, 242:84-89.
16. Lyamichev V, Mast A L, Hall J G, Prudent J R, Kaiser M W, Takova T, Kwiatkowski R W, Sander T J, de Arruda M, Arco DA, et al.: Polymorphism identification and quantitative detection of genomic DNA by invasive cleavage of oligonucleotide probes. *Nat Biotechnol* 1999, 17:292-296.
17. Griffin T J, Hall J G, Prudent J R, Smith L M: Direct genetic analysis by matrix-assisted laser desorption/ionization mass spectrometry. *Proc Natl Acad Sci USA* 1999, 96:6301-6306.
18. Heid C A, Stevens J, Livak K J, Williams P M: Real time quantitative PCR. *Genome Res* 1996, 6:986-994.
19. Tyagi S, Kramer F R: Molecular beacons: probes that fluoresce upon hybridization. *Nat Biotechnol* 1996, 14:303-308.
20. Mashal R D, Koontz J, Sklar J: Detection of mutations by cleavage of DNA heteroduplexes with bacteriophage resolvases. *Nat Genet* 1995, 9:177-183.

The invention claimed is:

1. A method of enriching a preselected nucleic acid from a mixture of nucleic acids, the preselected nucleic acid encompassing a sequence variant at a given position, the method comprising the steps of:
   (a) providing a mixture of nucleic acids which includes the preselected nucleic acid to be enriched;
   (b) cleaving the nucleic acids in the mixture to provide a nucleic acid fragment comprising the preselected nucleic acid, wherein the sequence variant is located 3' of the 5' end of the fragment, and denaturing the fragment if the fragment is at least partially double stranded;
   (c) providing a template oligonucleotide, wherein one end of the template oligonucleotide hybridizes to a downstream sequence beginning at the 3' end of the fragment and the other end of the template oligonucleotide hybridizes to an upstream sequence of the fragment which is 5' of the downstream sequence and which is 3' of the 5' end of the fragment, and wherein the sequence variant is located in the upstream sequence;
   (d) hybridizing the template oligonucleotide to said downstream sequence and to said upstream sequence such that said 3' end of the fragment and the upstream sequence are brought into juxtaposition with each other, optionally with a gap therebetween filled by a complementary oligonucleotide or by extension of the upstream sequence or the downstream sequence, and such that a protruding sequence at the 5' end of the fragment that is a substrate for a structure specific enzyme is generated;
   (e) cleaving the substrate with a structure specific enzyme, wherein only the protruding sequence is removed;
   (f) after cleavage by the structure specific enzyme, joining said 3' end of the fragment to the 5' end of the fragment, optionally with the complementary oligonucleotide or extension therebetween, to form a circularized ligated-product containing the preselected nucleic acid, which circularized ligated-product is protected from degradation; and
   (g) enriching for the ligated product by degrading unligated product and/or amplifying the circularized ligated-product.

2. A method according to claim 1, wherein cleavage of the substrate with the structure specific enzyme results in the sequence variant being located at the 5' end of the fragment.

3. The method according to claim 1, wherein, in step (g), said degrading is effected with an exonuclease enzyme.

4. The method according to claim 1, wherein the structure specific enzyme has 5' exonuclease activity and is selected from the group consisting of:
   Native or recombinant Fen nuclease,
   Native or recombinant Mja nuclease,
   Recombinant polymerase from *Thermus aquaticus*,
   Native or recombinant polymerase from *Thermus thermophilus*, and
   Native or recombinant polymerase from *Thermus flavus*.

5. The method according to claim 1, wherein the structure specific enzyme is native polymerase from *Thermus aquaticus*.

6. The method according to claim 1, wherein, in step (g), said amplifying comprises rolling circle amplification.

7. The method according to claim 1, wherein, in step (b), cleavage of the nucleic acids uses at least one adapter and at least one restriction enzyme.

8. The method according to claim 1, wherein, when the nucleic acid fragment is hybridized to the template oligonucleotide, there is a gap between the hybridized downstream sequence and the hybridized upstream sequence.

9. The method according to claim 8, wherein one of the hybridized downstream sequence and the hybridized upstream sequence is extended to fill the gap therebetween.

10. The method according to claim 9, wherein one of the hybridized downstream sequence and the hybridized upstream sequence is extended with a polymerase.

11. The method according to claim 10, wherein the extended sequence is extended with an enzyme selected from the group consisting of:
Native or recombinant polymerase from *Thermus aquaticus*,
Native or recombinant polymerase from *Thermus thermophilus*, and
Native or recombinant polymerase from *Thermus flavus*.

12. The method according to claim 8, wherein one of the hybridized downstream sequence and the hybridized upstream sequence is extended with Klenow.

13. The method according to claim 8, wherein the gap is filled by a complementary oligonucleotide.

14. The method according to claim 13, wherein the complementary oligonucleotide inserted into the gap is labelled with an affinity tag.

15. The method according to claim 14, wherein the complementary oligonucleotide is labelled with biotin.

16. The method according to claim 1, further comprising, prior to cleaving the nucleic acids in step (b), an initial step of denaturing the nucleic acid if the nucleic acid is at least partially double stranded.

17. The method according to claim 6, in which amplification is performed with native or recombinant polymerase of phage phi29.

18. The method according to claim 1, wherein the sequence variant is a single nucleotide polymorphism.

19. The method according to claim 1, wherein the sequence variant is a single nucleotide variant.

20. The method according to claim 1, wherein the sequence variant is a deletion variant.

21. The method according to claim 1, wherein the sequence variant is an insertion variant.

22. The method according to claim 1, wherein the sequence variant is a sequence length variation.

23. A method of enriching a preselected nucleic acid from a mixture of nucleic acids, the method comprising the steps of:
(a) providing a mixture of nucleic acids which includes the preselected nucleic acid to be enriched;
(b) cleaving the nucleic acids in the mixture to provide a nucleic acid fragment comprising the preselected nucleic acid, and denaturing the fragment if the fragment is at least partially double stranded;
(c) providing a template oligonucleotide, wherein one end of the template oligonucleotide hybridizes to a downstream sequence beginning at the 3' end of the fragment and the other end of the template oligonucleotide hybridizes to an upstream sequence of the fragment which is 5' of the downstream sequence and which is 3' of the 5' end of the fragment;
(d) hybridizing the template oligonucleotide to said downstream sequence and to said upstream sequence such that said 3' end of the fragment and the upstream sequence are brought into juxtaposition with each other, optionally with a gap therebetween filled by a complementary oligonucleotide or by extension of the upstream sequence or the downstream sequence, and such that a protruding sequence at the 5' end of the fragment that is a substrate for a structure specific enzyme is generated;
(e) cleaving the substrate with a structure specific enzyme, wherein only the protruding sequence is removed;
(f) after cleavage by the structure specific enzyme, joining said 3' end of the fragment to the 5' end of the fragment, optionally with the complementary oligonucleotide or extension therebetween, to form a circularized ligated-product containing the preselected nucleic acid, which circularized ligated-product is protected from degradation; and
(g) enriching for the ligated product by degrading unligated product and/or amplifying the circularized ligated-product.

24. The method according to claim 23, wherein, in step (g), said degrading is effected with an exonuclease enzyme.

25. The method according to claim 23, wherein the structure specific enzyme has 5' exonuclease activity and is selected from the group consisting of:
Native or recombinant Fen nuclease,
Native or recombinant Mja nuclease,
Recombinant polymerase from *Thermus aquaticus*,
Native or recombinant polymerase from *Thermus thermophilus*, and
Native or recombinant polymerase from *Thermus flavus*.

26. A method according to claim 23, wherein the structure specific enzyme is native polymerase from *Thermus aquaticus*.

27. The method according to claim 23, wherein, in step (g), said amplifying comprises rolling circle amplification.

28. The method according to claim 23, wherein amplification is performed with native or recombinant polymerase of phage phi29.

29. The method according to claim 23, wherein, in step (b), cleavage of the nucleic acids uses at least one adapter and at least one restriction enzyme.

30. The method according to claim 23, wherein, when the nucleic acid fragment is hybridised to the template oligonucleotide, there is a gap between the hybridized downstream sequence and the hybridized upstream sequence.

31. The method according to claim 30, wherein one of the hybridized downstream sequence and the hybridized upstream sequence is extended to fill the gap therebetween.

32. The method according to claim 31, wherein one of the hybridized downstream sequence and the hybridized upstream sequence is extended with a polymerase.

33. The method according to claim 32, wherein the extended sequence is extended with an enzyme selected from the group consisting of:
Native or recombinant polymerase from *Thermus aquaticus*,
Native or recombinant polymerase from *Thermus thermophilus*, and
Native or recombinant polymerase from *Thermus flavus*.

34. The method according to claim 31, wherein one of the hybridized downstream sequence and the hybridized upstream sequence is extended with Klenow.

35. The method according to claim 30, wherein the gap is filled by a complementary oligonucleotide.

36. The method according to claim 35, wherein the complementary oligonucleotide inserted into the gap is labelled with an affinity tag.

37. The method according to claim 36, wherein the complementary oligonucleotide is labelled with biotin.

38. The method according to claim 23, further comprising, prior to cleaving the nucleic acids in step (b), an initial step of denaturing the nucleic acid if the nucleic acid is at least partially double stranded.

39. The method according to claim 23, wherein, in step (g), the amplification product is labelled during amplification.

40. The method according to claim 23, wherein the preselected nucleic acid is subjected to a further step of nucleotide sequencing.

41. The method according to claim 23, wherein the enriched ligated product of step (g) is subjected to a further step of quantification.

42. The method according to claim 1, wherein the protruding sequence comprises the portion of the fragment which is 5' of the upstream sequence, and after cleavage by the structure specific enzyme, the upstream sequence is at the 5' end of the resulting cleaved fragment.

* * * * *

SEQUENCE LISTING

<160> NUMBER OF SEQ ID NOS: 18

<210> SEQ ID NO 1
<211> LENGTH: 46
<212> TYPE: DNA
<213> ORGANISM: Artificial
<220> FEATURE:
<223> OTHER INFORMATION: Ligation template oligonucleotide

<400> SEQUENCE: 1
tttttttttt ttttgtctg gaaagcaaac cggtgccac ccatga        46

<210> SEQ ID NO 2
<211> LENGTH: 15
<212> TYPE: DNA
<213> ORGANISM: Artificial
<220> FEATURE:
<223> OTHER INFORMATION: PCR primer

<400> SEQUENCE: 2
acgcccacgg ctgtc        15

```
<210> SEQ ID NO 3
<211> LENGTH: 19
<212> TYPE: DNA
<213> ORGANISM: Artificial
<220> FEATURE:
<223> OTHER INFORMATION: PCR Primer

<400> SEQUENCE: 3
tggacgtctg gaaagcaaa                                                  19

<210> SEQ ID NO 4
<211> LENGTH: 35
<212> TYPE: DNA
<213> ORGANISM: Artificial
<220> FEATURE:
<223> OTHER INFORMATION: FokI cleavage adapter

<400> SEQUENCE: 4
cgcatcccac gtgggatgcg aaagcaaaca ggggt                                35

<210> SEQ ID NO 5
<211> LENGTH: 36
<212> TYPE: DNA
<213> ORGANISM: Artificial
<220> FEATURE:
<223> OTHER INFORMATION: FokI cleavage adapter

<400> SEQUENCE: 5
gccatccgtg cacggatggc tgcacagcac cgtgat                               36

<210> SEQ ID NO 6
<211> LENGTH: 36
<212> TYPE: DNA
<213> ORGANISM: Artificial
<220> FEATURE:
<223> OTHER INFORMATION: FokI cleavage adapter

<400> SEQUENCE: 6
gccatccgtg cacggatggc tgcacagcac catgat                               36

<210> SEQ ID NO 7
<211> LENGTH: 43
<212> TYPE: DNA
<213> ORGANISM: Artificial
<220> FEATURE:
<223> OTHER INFORMATION: Ligation template oligonucleotide

<400> SEQUENCE: 7
ctcggctcta aagcaaacag gtgatggacg tctggaaagc ttt                       43

<210> SEQ ID NO 8
<211> LENGTH: 43
<212> TYPE: DNA
<213> ORGANISM: Artificial
<220> FEATURE:
<223> OTHER INFORMATION: Ligation template oligonucleotide

<400> SEQUENCE: 8
ctcggctcta aagcaaacag atgatggacg tctggaaagc ttt                       43

<210> SEQ ID NO 9
<211> LENGTH: 21
<212> TYPE: DNA
<213> ORGANISM: Artificial
<220> FEATURE:
<223> OTHER INFORMATION: PCR primer
```

<400> SEQUENCE: 9
cagaggtgat catccggttt g                                         21

<210> SEQ ID NO 10
<211> LENGTH: 20
<212> TYPE: DNA
<213> ORGANISM: Artificial
<220> FEATURE:
<223> OTHER INFORMATION: PCR primer

<400> SEQUENCE: 10
ggagaggagg cgcagagtgt                                           20

<210> SEQ ID NO 11
<211> LENGTH: 23
<212> TYPE: DNA
<213> ORGANISM: Artificial
<220> FEATURE:
<223> OTHER INFORMATION: Upstream primer oligonucleotide

<400> SEQUENCE: 11
gtatttgctg ggcactcact gca                                       23

<210> SEQ ID NO 12
<211> LENGTH: 34
<212> TYPE: DNA
<213> ORGANISM: Artificial
<220> FEATURE:
<223> OTHER INFORMATION: Downstream oligonucleotide

<400> SEQUENCE: 12
tccagacgtc catcacggtg ctgtgcattg cctg                           34

<210> SEQ ID NO 13
<211> LENGTH: 34
<212> TYPE: DNA
<213> ORGANISM: Artificial
<220> FEATURE:
<223> OTHER INFORMATION: Downstream oligonucleotide

<400> SEQUENCE: 13
tccagacgtc catcatggtg ctgtgcattg cctg                           34

<210> SEQ ID NO 14
<211> LENGTH: 42
<212> TYPE: DNA
<213> ORGANISM: Artificial
<220> FEATURE:
<223> OTHER INFORMATION: Template oligonucleotide

<400> SEQUENCE: 14
caggcaatgc acagcaccgt gcagtgagtg cccagcaaat ac                  42

<210> SEQ ID NO 15
<211> LENGTH: 27
<212> TYPE: DNA
<213> ORGANISM: Artificial
<220> FEATURE:
<223> OTHER INFORMATION: DraIII cleavage adapter

<400> SEQUENCE: 15
actggacaca acgtgacgaa cttgggt                                   27

```
<210> SEQ ID NO 16
<211> LENGTH: 25
<212> TYPE: DNA
<213> ORGANISM: Artificial
<220> FEATURE:
<223> OTHER INFORMATION: DraIII cleavage adapter

<400> SEQUENCE: 16
cagggctcac acgcagtgag tgccc                                              25

<210> SEQ ID NO 17
<211> LENGTH: 38
<212> TYPE: DNA
<213> ORGANISM: Artificial
<220> FEATURE:
<223> OTHER INFORMATION: Ligation template oligonucleotide

<400> SEQUENCE: 17
taaacgaccc gtgagtgacg cacaggtcac gggggac                                 38

<210> SEQ ID NO 18
<211> LENGTH: 38
<212> TYPE: DNA
<213> ORGANISM: Artificial
<220> FEATURE:
<223> OTHER INFORMATION: Ligation template oligonucleotide

<400> SEQUENCE: 18
taaacgaccc gtgagtgacg gacaggtcac gggggac                                 38
```